United States Patent
Jaser et al.

(10) Patent No.: US 6,513,727 B1
(45) Date of Patent: Feb. 4, 2003

(54) LIQUID ATOMIZER DEVICE

(75) Inventors: Stefan Jaser, Bobingen (DE); Matthias Remke, Starnberg (DE); Stephan Brugger, Starnberg (DE)

(73) Assignee: Pari GmbH Spezialisten fureffektive Inhalation, Starnberg (DE)

( * ) Notice: Subject to any disclaimer, the term of this patent is extended or adjusted under 35 U.S.C. 154(b) by 0 days.

(21) Appl. No.: 09/333,429

(22) Filed: Jun. 15, 1999

(30) Foreign Application Priority Data

Jun. 18, 1998 (DE) .......................................... 198 27 228

(51) Int. Cl.$^7$ ................................................ B67D 5/08
(52) U.S. Cl. ........................ 239/71; 239/338; 239/370
(58) Field of Search ................................. 239/338, 370, 239/71; 128/200.11–200.21

(56) References Cited

U.S. PATENT DOCUMENTS 5,312,046 A * 5/1994 Knoch et al. ............... 239/338
5,679,442 A 10/1997 Haindl
5,957,389 A * 9/1999 Wunderlich et al. ........ 239/338

FOREIGN PATENT DOCUMENTS

DE 43 11 846 4/1993
EP 0 540 774 A1 5/1993

* cited by examiner

Primary Examiner—Robin O. Evans
(74) Attorney, Agent, or Firm—Merchant & Gould P.C.

(57) ABSTRACT

The present invention relates to a liquid atomizer device for producing aerosols. The device includes a first housing part (A) which includes an inner member (3) of an atomizer nozzle and a first connection for connecting the first housing part (A) to a further housing part to form a nebulizing chamber (1), and further includes a second housing part (B) that includes an outer member of the atomizer nozzle which can be brought into engagement with the inner member (3) to form the atomizer nozzle, and a second connection means (11) that can be brought into engagement with the first connection (9) for connecting the second housing part to the first housing part. The invention is characterized in that a service life indicator (L) is arranged at a place that does not impede the flow passing through the device, but is accessible to the aerosol and a sterilant.

1 Claim, 3 Drawing Sheets

LIQUID ATOMIZER DEVICE

BACKGROUND OF THE INVENTION

The present invention relates to a liquid atomizer device.

Such a liquid atomizer device is known from EP-A1-540774. The liquid atomizer device for producing an aerosol is especially used for inhalation purposes. Such devices must be sterilized after use. One possibility of sterilization is steam sterilization during which, however, the problem arises that the service life of the steam-sterilizable devices is limited. There is consequently the risk that the devices will fail during use after repeated sterilization. Disadvantageous consequences thereof might e.g. be the breaking of functionally essential parts, possibly resulting in a failure of the liquid atomizer device.

To solve said problem, DE 4311846 C1 discloses a service life indicator for repeatedly sterilizable plastic products which contains a color pigment that intermolecularly diffuses into the polymer material of the indicator in dependence upon the temperature. Since the diffusible pigment deeply penetrates into the polymer, it cannot be removed or impaired by cleaning processes performed on the surface. The display in the life indicator known from DE 4311846 C1 is such that during every steam sterilization the pigment will slightly diffuse to a further degree when pigment and polymer are correctly adjusted to each other. This has the effect that with each sterilization the pigment becomes paler, first in an unnoticeable and then in a noticeable manner. When polymer and pigment are suitably adjusted, the pigmentation will disappear after about hundred sterilization processes.

Despite the fact that said service life indicator has been known, its use in liquid atomizer devices has so far not been taken into consideration because in liquid atomizer devices the material of the device may be influenced not only by the sterilization but also by the liquid to be atomized and by the gas, in particular air, which is required for the atomization. Furthermore, the use of the known service life indicator in liquid atomizer devices has not been taken into consideration because the flow conditions in such devices are very complicated to ensure an optimum atomization. Therefore, it has been assumed that the mounting of the indicator would have a negative effect on the flow conditions and thus on the aerosol formation.

SUMMARY OF THE INVENTION

It is therefore the object of the present invention to provide a liquid atomizer device comprising a service life indicator that is used to avoid a premature disposal, but does not affect the aerosol formation.

Since the service life indicator is mounted at a place that does not impede the passage of the flow, but which may come into contact with both the aerosol to be produced and the sterilant, this has the effect that influences that might be exerted by the aerosol to be formed on the material of the liquid atomizer device of the invention and also by the sterilant are sensed by the service life indicator and thus can be indicated. Investigations conducted within the scope of the invention have shown that for the first time it has been possible by virtue of this special mounting to successfully use the service life indicator, which is per se known, in a liquid atomizer device for producing aerosols.

In a preferred embodiment of the liquid atomizer device according to the invention, the service life indicator is arranged in the housing so that it is protected against damage caused by externally acting forces, e.g. when the device is handled.

To fasten the service life indicator in an easy manner, the service life indicator may be mounted on a nebulizing chamber divider. In the disassembled state of the liquid atomizer device said nebulizing chamber divider is easily accessible and clearly visible, so that the service life indicator immediately will be perceived by the operator.

Furthermore, the service life indicator preferably is mounted either at the bottom side of a baffle section or at the upper side of the baffle section of the nebulizing chamber divider. As a result, the mounting of the service life indicator is further simplified and the indicator can be perceived clearly at the same time.

In a further preferred embodiment of the present invention the service life indicator is designed as a portion of a first housing part or of a second housing part. An additional component in the form of a separate service life indicator is thus not necessary so that the assembly of the liquid atomizer device of the invention is simplified. Nor is there any risk that the service life indicator is unintentionally separated or gets detached from the liquid atomizer device of the invention, so that during further use of the liquid atomizer device an indication of the service life is no longer given.

To prevent any unintentional detachment of the service life indicator from the liquid atomizer device, the service life indicator is integrally connected to the portion of the first holding part and/or of the second housing part.

In an alternative embodiment the handle of the liquid atomizer device comprises a service life indicator positioned within the housing. It is thereby possible to first secure the service life indicator to the end of the handle which faces the housing of the liquid atomizer device and then to insert and secure the handle into and to the housing so that the service life indicator is again arranged at a place accessible to the aerosol and the sterilant.

To counteract the effect of the flow passing through the device when the service life indicator is formed on the handle, the service life indicator may be provided with a flow guiding surface. This flow guiding surface permits an optimum guidance of the flow within the liquid atomizer device towards the suction nozzle of the liquid atomizer device.

Finally, to avoid an operation in which the service life indicator is mounted on the handle, the service life indicator may be made integral with the handle.

BRIEF DESCRIPTION OF THE DRAWINGS

Further details, features and advantages of the present invention will become apparent from the following description of embodiments taken in conjunction with the drawing, in which.

DETAILED DESCRIPTION

Figure 1:
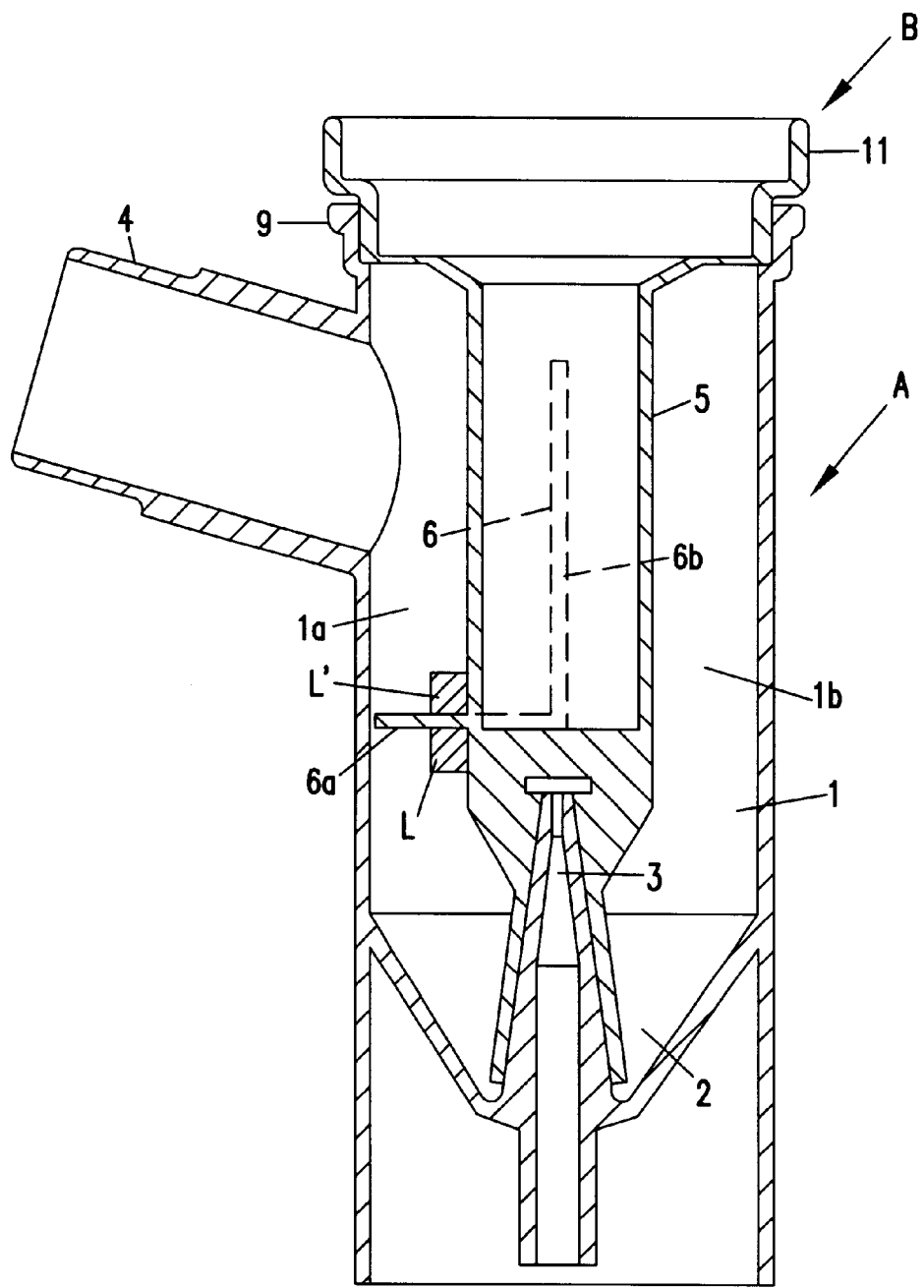
FIG. 1 is a schematic view of a liquid atomizer device according to the invention with a service life indicator.

FIG. 1 schematically shows a liquid atomizer device according to the invention for producing aerosols. The liquid atomizer device includes two housing parts A, B, which can be brought into engagement with each other by respective connection means 9, 11. The housing part A comprises a substantially cylindrical nebulizing chamber 1. In FIG. 1 the nebulizing chamber 1 is downwardly closed by a liquid collection portion 2 into which a liquid can be filled. The liquid is atomized with the aid of an atomizer nozzle having an inner member 3 so that a liquid mist is formed in the nebulizing chamber 1. The liquid mist is sucked via a suction nozzle 4 of the housing part A out of the nebulizing chamber 1. To provide the respiratory air required therefor, the second housing part B is arranged centrally with a cylindrical supply air chimney 5 inside the nebulizing chamber. The supply air chimney 5 is upwardly and downwardly open in FIG. 1. As a result, most of the air withdrawn via the suction nozzle 4 is passed through the supply air chimney 5 into the nebulizing chamber 1. The lower end of the supply air chimney 5 which projects into the nebulizing chamber is located in the direct vicinity of the atomizing end of the atomizer nozzle to achieve a satisfactory homogenization of the liquid mist.

In the present invention the mixing and homogenizing operation is supported by a nebulizing chamber divider 6. The nebulizing chamber divider 6 separates a part 1a of the nebulizing chamber 1, which is positioned in direct vicinity of the opening of the suction nozzle 4, from the remaining part 1b of the nebulizing chamber 1. Both parts 1a and 1b are connected to each other such that it is still possible to suck the liquid mist out of the nebulizing chamber 1 via the suction nozzle 4.

In the present embodiment of the liquid atomizer device, the nebulizing chamber divider 6 includes a baffle section 6a and guide sections 6b. The baffle section 6a serves to remove large liquid drops. As a consequence, large liquid drops can no longer be sucked via the suction nozzle 4 or can only be sucked to a small degree. By contrast, the guide sections 6b have the effect that the air flow adjusted by the supply air chimney 5 flows along the guide sections 6b and through the connection portion above the guide sections 6b towards the opening of the suction nozzle 4. To this end the guide sections 6b are designed such that they extend substantially in a direction perpendicular to the baffle section 6a and in the axial direction of the cylindrical nebulizing chamber 1.

Furthermore, a service life indicator L is mounted in FIG. 1 on the bottom side of the baffle section 6a. The service life indicator L thus is consequently positioned at a place that does not impede the flow passing through the liquid atomizer device, but is accessible to the aerosol and a sterilant, for the two housing parts A and B are separated from each other during sterilization so that the service life indicator L is freely accessible to the sterilant.

A life indicator L', which in FIG. 1 is positioned on the upper side of the baffle plate 6a, is drawn in FIG. 1 as an alternative. This service life indicator also meets the demands made with respect to an aerosol and the sterilant.

Although FIG. 1 shows two service life indicators L, L', the two indicators are only to be understood as alternatives, so that of course only one service life indicator must be provided in the liquid atomizer device of the invention for producing aerosols.

Figure 2:
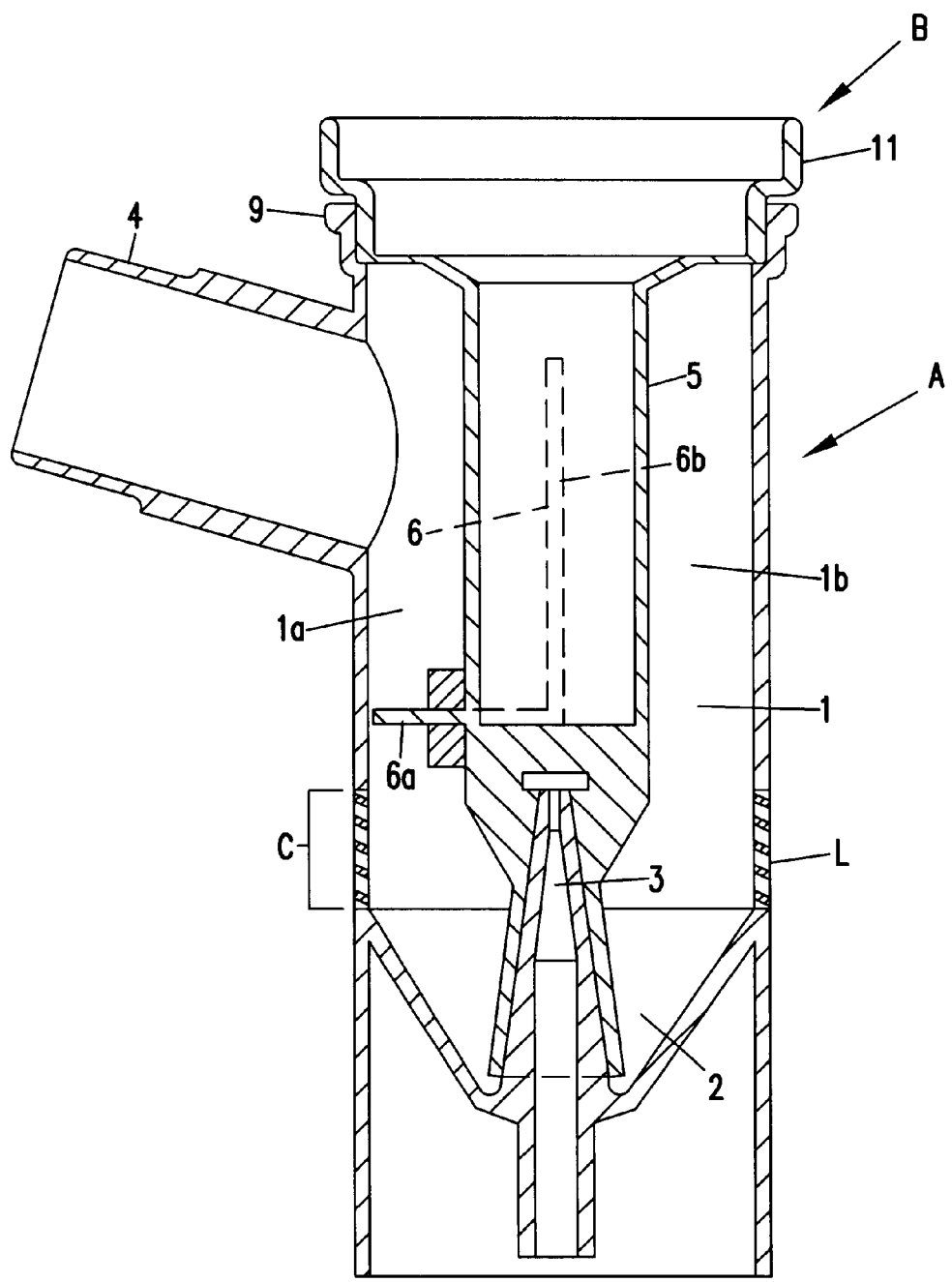
FIG. 2 is a view similar to FIG. 1, but the service life indicator is an integral part of the housing.

FIG. 2 shows an alternative embodiment of the liquid atomizer device according to the invention. FIG. 2 differs from FIG. 1 by the feature that no service life indicator is mounted on the baffle plate 6a. In contrast, the housing part A comprises a portion C which is designed as a service life indicator L. In the present embodiment, the portion C is connected integrally to the housing part A. Alternatively, the service life indicator L of course also can be made integral with the housing part B. Other portions of the housing part A also are suited for a design as a service life indicator. For instance, the portion of the housing part A which in FIG. 2 is located above the suction nozzle 4 can be designed as a service life indicator. Moreover, it is possible subsequently to insert the service life indicator L in the embodiment according to FIG. 2. Although such a subsequent insertion increases the production costs of a liquid atomizer device, it is possible to retrofit already existing liquid atomizer devices with service life indicators.

Figure 3:
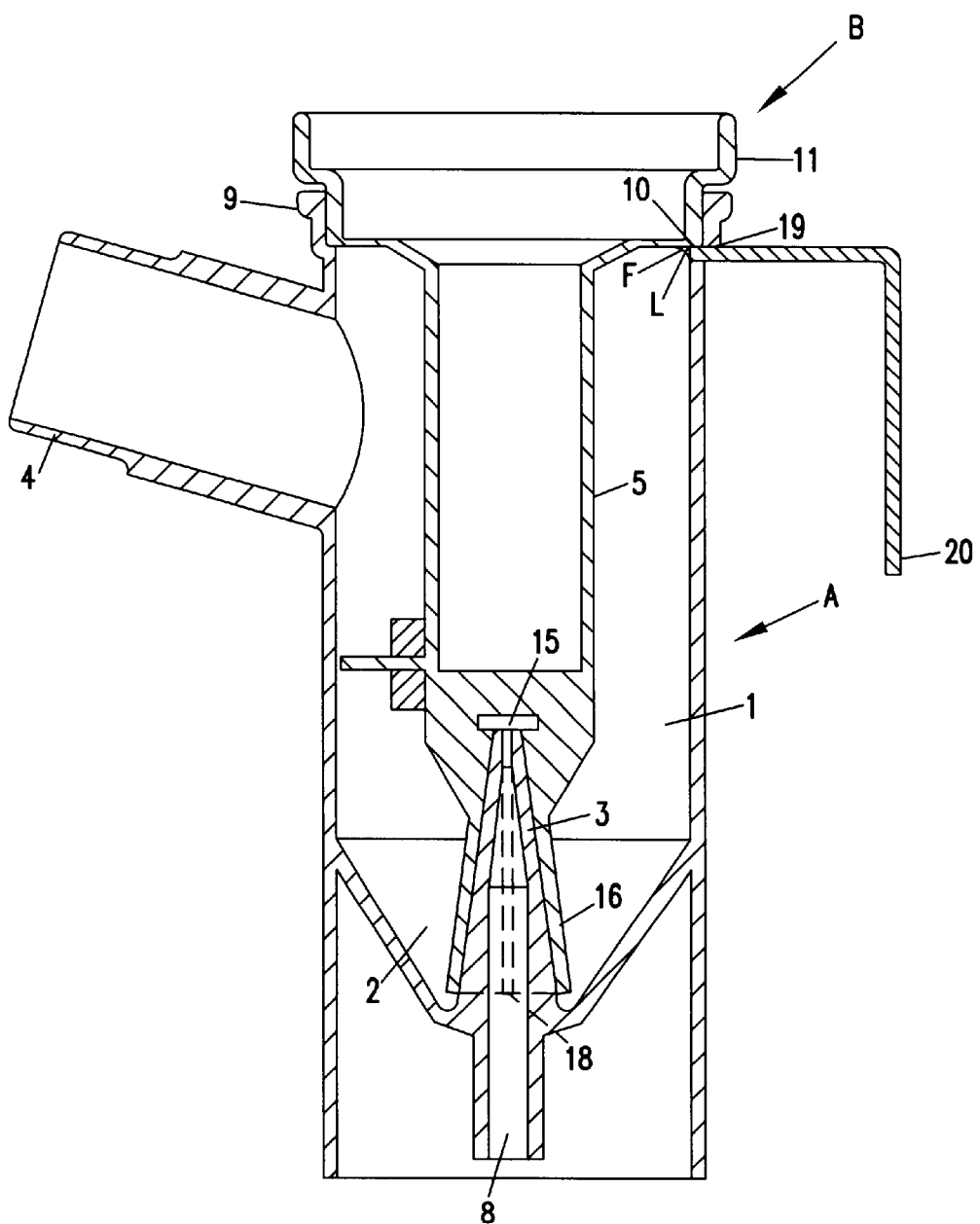
FIG. 3 shows an alternative embodiment of the liquid atomizer device according to the invention with a service life indicator mounted on a handle.

Finally, FIG. 3 shows a further embodiment of the liquid atomizer device according to the invention. In contrast to the embodiments shown in FIGS. 1 and 2, the atomizer nozzle includes an inner member 3 and an outer member 16. The inner member 3 of the atomizer nozzle is made integral with the aerosol suction nozzle 4. Moreover, the inner member 3 of the atomizer nozzle is preferably designed as a pointed hollow member and its end outside the nebulizing chamber 1 comprises a connection, for example for a compressed gas line through which the pressurized gas, most of the time air, is supplied to a compressed air channel in the inner member 3 of the atomizer nozzle. Furthermore, a first connection means 9 is provided at the end of the first housing part A, which is opposite to the liquid collection portion 2. Moreover, the first housing part A comprises a first stop surface 10 that cooperates with the second housing part B.

The supply air chimney 5, which in accordance with FIGS. 1 and 2 is upwardly and downwardly open, is made integral with the second connection means 11. Furthermore, the bottom end of the supply air chimney 5 has formed thereon a gas-flow control surface that extends in a direction transverse to the substantially circular opening of the supply air chimney 5. The outer member 16 of the atomizer nozzle, which is joined with the inner member 3 of the atomizer nozzle, is located outside the gas-flow control surface 15. The inner wall of the outer member 16 of the atomizer nozzle is shaped in conformity with the form of the inner member 3 of the atomizer nozzle. Furthermore, the inner wall comprises at least one, but preferably two diametrically opposed grooves 18 that form the liquid channels. When two grooves 18 are provided, these preferably should be arranged at both sides of the gas-flow control surface 15 in such a manner that a straight connection line extends between the grooves in a direction perpendicular to the plane of the gas-flow control surface 15.

Finally, an opening 19 is provided in the housing part A below the stop surface 10 of the housing part B. This opening 19, in turn, is engaged by a handle 20. The service life indicator L is secured to the end of the handle 20 that extends into the opening 19 of the housing part A. The service life indicator L is here provided with a curved surface F, which serves as a flow guiding surface. This surface F permits an improved flow guidance of the atomized gas to the suction nozzle 4, thereby preventing a negative effect on the flow conditions.

Although this cannot be seen in the schematic illustration of FIG. 3, the handle 20 is made integral with the service life indicator L. Of course, as an alternative, the service life indicator can be secured to the handle 20 at a later time and the handle 20 can be secured to the housing part A. Moreover, with a corresponding construction of the liquid atomizer device, a flow guiding surface F need not be provided on the service life indicator L.

Although the liquid atomizer devices are shown in FIGS. 1 and 2 without a handle 20, it is of course possible to provide these two embodiments with a handle. Of course, this is also applicable to the service life indicator L secured to the handle 20. Inversely, the service life indicators L described in conjunction with FIGS. 1 and 2 can of course be used in the embodiment of the liquid atomizer device according to FIG. 3, instead of the service life indicator described in said figure.

What is claimed is:

1. A liquid atomizer device for producing aerosols, comprising:

a housing;

an atomizer disposed in a nebulizing chamber in the housing;

a handle comprising a portion that extends into the housing, the portion of the handle in the housing comprising a service life indicator that is provided with a flow guiding surface.

\* \* \* \* \*